(12) United States Patent
Melsheimer et al.

(10) Patent No.: US 7,811,238 B2
(45) Date of Patent: Oct. 12, 2010

(54) WIRE GUIDE HAVING DISTAL COUPLING TIP

(75) Inventors: Jeffry S. Melsheimer, Springville, IN (US); Christopher L. Hruska, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 0 days.

(21) Appl. No.: 11/652,430

(22) Filed: Jan. 11, 2007

(65) Prior Publication Data

US 2007/0167065 A1    Jul. 19, 2007

Related U.S. Application Data

(60) Provisional application No. 60/758,880, filed on Jan. 13, 2006.

(51) Int. Cl.
*A61M 25/00* (2006.01)
(52) U.S. Cl. ..................................... 600/585
(58) Field of Classification Search ............... 600/585; 604/535, 103.04, 528, 264, 113
See application file for complete search history.

(56) References Cited

U.S. PATENT DOCUMENTS

| | | | |
|---|---|---|---|
| 2,657,691 A | 11/1953 | Nordstrom, Jr. | |
| 3,521,620 A | 7/1970 | Cook | |
| 3,547,103 A | 12/1970 | Cook | |
| 3,656,680 A | 4/1972 | Nomura | |
| 3,890,997 A | 6/1975 | Wilson | |
| 4,548,206 A | 10/1985 | Osborne | |
| 4,569,347 A | 2/1986 | Frisbie | |
| 4,601,713 A | 7/1986 | Fuqua | |
| 4,650,472 A | 3/1987 | Bates | |
| 4,665,906 A | 5/1987 | Jervis | |
| 4,824,435 A * | 4/1989 | Giesy et al. | ............ 604/500 |
| 4,921,483 A | 5/1990 | Wijay et al. | |
| 4,925,445 A | 5/1990 | Sakamoto et al. | |
| 4,934,380 A | 6/1990 | De Toledo | |
| 4,984,581 A | 1/1991 | Stice | |

(Continued)

FOREIGN PATENT DOCUMENTS

EP    0 436 303 A1    11/1990

(Continued)

OTHER PUBLICATIONS

The Journal of Invasive Cardiology entitled "Use of a Second Buddy Wire During Percutaneous Coronary Interventions: A Simple Solution for Some Challenging Situations" dated Apr. 25, 2005, pp. 1-8.

(Continued)

*Primary Examiner*—Max Hindenburg
*Assistant Examiner*—Michael C Stout
(74) *Attorney, Agent, or Firm*—Brinks Hofer Gilson & Lione

(57) ABSTRACT

A coupling wire guide structured to be slidably coupled to a previously introduced wire guide. The coupling wire guide includes a main body having a distal section. The distal section includes an outer wire disposed over a safety wire. A loop wire is connected to the safety wire at two axially spaced points. At least a portion of the loop wire is positioned outside of the outer wire to define a loop area sized to receive the previously introduced wire guide.

25 Claims, 7 Drawing Sheets

U.S. PATENT DOCUMENTS

| | | | |
|---|---|---|---|
| 5,003,990 A * | 4/1991 | Osypka | 600/585 |
| 5,046,497 A | 9/1991 | Millar | |
| 5,069,226 A | 12/1991 | Yamauchi et al. | |
| 5,105,818 A | 4/1992 | Christian et al. | |
| 5,129,890 A | 7/1992 | Bates et al. | |
| 5,131,407 A | 7/1992 | Ischinger et al. | |
| 5,159,861 A | 11/1992 | Anderson | |
| 5,213,111 A | 5/1993 | Cook et al. | |
| 5,242,759 A | 9/1993 | Hall | |
| 5,243,996 A | 9/1993 | Hall | |
| 5,251,640 A | 10/1993 | Osborne | |
| 5,267,958 A | 12/1993 | Buchbinder et al. | |
| 5,306,261 A | 4/1994 | Alliger et al. | |
| 5,318,527 A | 6/1994 | Hyde et al. | |
| 5,325,746 A | 7/1994 | Anderson | |
| 5,328,472 A | 7/1994 | Steinke et al. | |
| 5,328,480 A | 7/1994 | Milker et al. | |
| 5,344,413 A | 9/1994 | Allman et al. | |
| 5,354,257 A | 10/1994 | Roubin et al. | |
| 5,383,853 A * | 1/1995 | Jung et al. | 604/103.04 |
| 5,402,799 A | 4/1995 | Colon et al. | |
| 5,449,362 A | 9/1995 | Chaisson et al. | |
| 5,456,680 A | 10/1995 | Taylor et al. | |
| 5,488,959 A | 2/1996 | Ales | |
| 5,597,378 A | 1/1997 | Jervis | |
| 5,667,521 A | 9/1997 | Keown | |
| 5,738,667 A | 4/1998 | Solar | |
| 5,762,070 A * | 6/1998 | Nagamatsu | 600/564 |
| 5,776,079 A | 7/1998 | Cope et al. | |
| 5,776,100 A | 7/1998 | Forman | |
| 5,797,857 A | 8/1998 | Obitsu | |
| 5,810,876 A * | 9/1998 | Kelleher | 606/205 |
| 5,827,225 A | 10/1998 | Schwab | |
| 5,873,842 A | 2/1999 | Brennen et al. | |
| 5,882,333 A | 3/1999 | Schaer et al. | |
| 5,891,056 A | 4/1999 | Ramzipoor | |
| 5,893,868 A | 4/1999 | Hanson et al. | |
| 5,993,424 A | 11/1999 | Lorenzo et al. | |
| 5,997,526 A | 12/1999 | Giba et al. | |
| 6,007,517 A | 12/1999 | Anderson | |
| 6,139,510 A | 10/2000 | Palermo | |
| 6,217,567 B1 | 4/2001 | Zadno-Azizi et al. | |
| 6,221,066 B1 | 4/2001 | Ferrera et al. | |
| 6,254,549 B1 | 7/2001 | Ramzipoor | |
| 6,254,550 B1 | 7/2001 | McNamara et al. | |
| 6,290,693 B1 | 9/2001 | Jung, Jr. et al. | |
| 6,306,141 B1 | 10/2001 | Jervis | |
| 6,309,404 B1 * | 10/2001 | Krzyzanowski | 606/208 |
| 6,348,041 B1 | 2/2002 | Klint | |
| 6,383,146 B1 | 5/2002 | Klint | |
| 6,471,697 B1 | 10/2002 | Lesh | |
| 6,475,167 B1 | 11/2002 | Fleming et al. | |
| 6,500,130 B2 | 12/2002 | Kinsella et al. | |
| 6,502,606 B2 | 1/2003 | Klint | |
| 6,517,518 B2 | 2/2003 | Nash et al. | |
| 6,530,899 B1 * | 3/2003 | Savage | 604/103.04 |
| 6,569,151 B1 | 5/2003 | Nash et al. | |
| 6,596,963 B2 | 7/2003 | Kelly | |
| 6,605,049 B1 | 8/2003 | Wagner et al. | |
| 6,613,002 B1 | 9/2003 | Clark et al. | |
| 6,638,372 B1 | 10/2003 | Abrams et al. | |
| 6,682,608 B2 | 1/2004 | Abrams et al. | |
| 6,805,676 B2 | 10/2004 | Klint | |
| 6,872,192 B2 | 3/2005 | Nash et al. | |
| 7,074,197 B2 | 7/2006 | Reynolds et al. | |
| 7,076,285 B2 | 7/2006 | Windheuser et al. | |
| 7,229,431 B2 | 6/2007 | Houser et al. | |
| 7,527,606 B2 | 5/2009 | Oepen | |
| 2002/0058888 A1 * | 5/2002 | Biagtan et al. | 600/585 |
| 2002/0169457 A1 * | 11/2002 | Quinn | 606/108 |
| 2002/0193706 A1 * | 12/2002 | Ferrera | 600/585 |
| 2003/0028127 A1 | 2/2003 | Balzum et al. | |
| 2003/0120208 A1 | 6/2003 | Houser et al. | |
| 2004/0044350 A1 * | 3/2004 | Martin et al. | 606/139 |
| 2004/0073108 A1 | 4/2004 | Saeed et al. | |
| 2004/0116957 A1 | 6/2004 | Nishide | |
| 2004/0215208 A1 * | 10/2004 | Foushee et al. | 606/108 |
| 2005/0075647 A1 | 4/2005 | Walters et al. | |
| 2005/0143770 A1 | 6/2005 | Carter et al. | |
| 2005/0197663 A1 | 9/2005 | Soma et al. | |
| 2005/0209533 A1 * | 9/2005 | Lorenz | 600/585 |
| 2005/0267442 A1 | 12/2005 | Von Oepen | |
| 2005/0283122 A1 | 12/2005 | Nordgren | |
| 2006/0020256 A1 | 1/2006 | Bell et al. | |
| 2006/0100544 A1 | 5/2006 | Ayala et al. | |
| 2006/0100545 A1 | 5/2006 | Ayala et al. | |
| 2007/0060908 A1 * | 3/2007 | Webster et al. | 604/509 |
| 2007/0167065 A1 | 7/2007 | Melsheimer et al. | |
| 2007/0185414 A1 | 8/2007 | Urbanski et al. | |
| 2007/0191790 A1 | 8/2007 | Eells et al. | |

FOREIGN PATENT DOCUMENTS

| | | |
|---|---|---|
| EP | 0829269 A1 | 3/1998 |
| EP | 1057500 A1 | 12/2000 |
| EP | 1 428 546 A2 | 6/2004 |
| WO | WO 93/14805 | 8/1993 |
| WO | WO 96/10436 | 4/1996 |
| WO | WO 99/44510 | 9/1999 |
| WO | WO 00/74565 A1 | 12/2000 |
| WO | WO 01/03764 A1 | 1/2001 |
| WO | WO 02 094364 A2 | 11/2002 |
| WO | WO2004/033016 | 4/2004 |
| WO | WO 2004/049970 A2 | 6/2004 |
| WO | WO 2004/050161 A1 | 6/2004 |
| WO | WO 2005/011530 A1 | 2/2005 |
| WO | WO 2005/011788 A1 | 2/2005 |
| WO | WO 2005/025660 A1 | 3/2005 |
| WO | WO 2005/089852 A1 | 9/2005 |
| WO | WO 2006/039216 A2 | 4/2006 |
| WO | WO 2007/084474 A1 | 7/2007 |
| WO | WO 2007/089891 A1 | 8/2007 |
| WO | WO 2007/089893 A1 | 8/2007 |

OTHER PUBLICATIONS

International Search Report—PCT/US2006/040843 (Jan. 31, 2007).
International Search Report—PCT/US2007/002743 (Jun. 14, 2007).
International Search Report—PCT/US2007/002741 ( Jul. 9, 2007).
International Search Report & Written Opinion (Jan. 3, 2008).
Notification of Transmittal of International Preliminary Report on Patentability (Jan. 10, 2008).
International Search Report—PCT/US2006/042184 (Mar. 1, 2007).
International Search Report—PCT/US2007/001066 (Jun. 18, 2007).
International Search Report—PCT/US2007/004827 (Oct. 26, 2007).
Office Action dated Mar. 17, 2008, U.S. Appl. No. 11/706,548 issued in related application.
Office Action dated Apr. 7, 2008, U.S. Appl. No. 11/699,174 issued in related application.
Office Action dated May 16, 2008, U.S. Appl. No. 11/763,355 issued in related application.
Office Action dated May 30, 2008, U.S. Appl. No. 11/507,805 issued in related application.
International Search Report—PCT/US2007/04827 & Opinion (Mar. 14, 2008).
(Suppl) Notification of Transmittal of International Preliminary Report on Patentability—PCT/US2007/002743—(Jun. 3, 2008).
Office Action Restriction dated Mar. 3, 2008, U.S. Appl. No. 11/507,805 issued in related application.
Office Action Restriction dated Jul. 2, 2008, U.S. Appl. No. 11/699,171 issued in related application.
International Search Report/Written Opinion—PCT/US2006/040843 (Feb. 7, 2007).
International Preliminary Report on Patentability—PCT/US2007/002741 (Jun. 25, 2008).

International Preliminary Report on Patentability and Written Opinion (Jul. 24, 2008) PCT/US2007/001066.
Office Action dated Sep. 26, 2008, U.S. Appl. No. 11/706,548 issued in related application.
Office Action dated Oct. 7, 2008, U.S. Appl. No. 11/507,993 issued in related application.
Office Action dated Oct. 15, 2008, U.S. Appl. No. 11/699,174 issued in related application.
Office Action dated Mar. 30, 2009, U.S. Appl. No. 11/699,174 issued in co-pending application.
Office Action dated Apr. 1, 2009, U.S. Appl. No. 11/507,805 issued in co-pending application.
Office Action dated Apr. 7, 2009, U.S. Appl. No. 11/706,548 issued in co-pending application.
Office Action dated Apr. 14, 1009, U.S. Appl. No. 11/549,481 issued in co-pending application.
Office Action dated May 8, 2009, U.S. Appl. No. 11/699,171 issued in co-pending application.
Office Action dated May 14, 2009, U.S. Appl. No. 11/507,993 issued in coo-pending application.
Office Action dated Jun. 9, 2009, U.S. Appl. No. 11/763,355 issued in co-pending application.
Office Action dated Jun. 6, 2009, U.S. Appl. No. 11/699,174 issued in co-pending application.
Advisory Action dated Jun. 25, 2009, U.S. Appl. No. 11/549,481 issued in co-pending application.
Advisory Action dated Jun. 22, 2009, U.S. Appl. No. 11/706,548 issued in co-pending application.
Office Action dated Aug. 3, 2009, U.S. Appl. No. 11/699,174 issued in co-pending application.
Office Action dated Sep. 16, 2009, U.S. Appl. No. 11/549,481 issued in co-pending application.
Office Action dated Oct. 1, 2009, U.S. Appl. No. 11/763,355 issued in co-pending application.
Office Action dated Oct. 14, 2009, U.S. Appl. No. 11/507,805 issued in co-pending application.
Office Action dated Oct. 23, 2009, U.S. Appl. No. 11/706,548 issued in co-pending application.
Office Action dated Dec. 14, 2009, U.S. Appl. No. 11/507,993 issued in co-pending application.
Office Action dated Jan. 19, 2010, U.S. Appl. 11/699,171 issued in co-pending application.
Office Action dated Apr. 2, 2010, U.S. Appl. No. 11/507,805 issued in co-pending application.
Office Action dated Apr. 6, 2010, U.S. Appl. No. 11/763,355 issued in co-pending application.
Office Action dated Mar. 12, 2010, U.S. Appl. No. 11/699,174 issued in co-pending application.
Office Action dated Apr. 21, 2010, U.S. Appl. No. 11/706,548 issued in co-pending application.

* cited by examiner

WIRE GUIDE HAVING DISTAL COUPLING TIP

CROSS-REFERENCE TO RELATED APPLICATIONS

This application claims the benefit of U.S. Provisional Application Ser. No. 60/758,880 filed on Jan. 13, 2006, entitled "WIRE GUIDE HAVING DISTAL COUPLING TIP", the entire contents of which are incorporated herein by reference.

FIELD OF THE INVENTION

This invention relates generally to a wire guide for use in intracorporeal procedures, and more particularly relates to the construction of a wire guide to be coupled to a previously introduced wire guide for assistance during interventional procedures in vessels with proximal tortuosity, or as a more substantial wire guide for angioplasty procedures, stenting procedures, and other device placement procedures and their related devices.

BACKGROUND OF THE INVENTION

Proximal tortuosity of the vasculature is problematic for all medical catheter devices such as atherectomy devices, angioplasty devices, stent delivery devices, and filter delivery devices. Wire guides are therefore typically used to navigate the vasculature of a patient during percutaneous interventional procedures. Once the wire guide has been introduced, it may then be used to introduce one or more medical catheter devices. Thus, most wire guides are typically 0.014 inches in diameter and have a lubricious coating to enhance wire guide introduction movement. Conventional 0.014 inch floppy wire guides must have sufficient flexibility and torque control for navigation through tortuous vessels. At the same time, the wire guide must have a certain amount of rigidity to pass through lesions, straighten extremely tortuous vessels, and support medical catheter devices that are introduced over the wire guide.

Accordingly, wire guides are subjected to potentially conflicting requirements. Conventional 0.014 inch floppy wire guides are usually sufficient for navigation of moderately tortuous vessels. However, in some situations the wire guide tip may prolapse away from the site to which it is guiding the device. For example, balloon angioplasty in vessels with proximal tortuosity has been associated with a higher incidence of acute complications and procedural failure due to the inability to cross lesions with a conventional floppy wire guide, and due to the inability of the wire guide to provide adequate support to the balloon catheter. Heavy-duty wire guides, on the other hand, are generally not well suited as primary wire guides because of their stiffness and potential for causing injury to the vessel during introduction.

It may therefore be desirable to use conventional floppy wire guides for navigation of tortuous vessels, and then enhance the conventional wire guide with a supplemental wire guide. The supplemental wire guide will straighten out the vessel curves and ease further wire guide movement. Additionally, the supplemental wire guide provides greater support and enhances the tracking of balloons, stents, stent delivery devices, atherectomy devices, and other medical catheter devices as compared to a conventional floppy wire guide. This technique is commonly referred to as the "Buddy Wire" technique, details of which are disclosed in U.S. patent application Ser. No. 11/081,146, filed Mar. 16, 2005.

However, the navigation of the supplemental wire guide parallel to the first wire guide is an exacting and time consuming process in which additional difficulties are encountered. For example, the second wire guide can cork screw or coil around the first wire guide, which may result in immobilization or unintended movement of the first wire guide, which in turn may require the retraction and re-feeding of the supplemental wire guide and/or the primary wire guide. Moreover, if retraction of the supplemental wire guide is necessary, either of the wire guides may become contaminated and the entire process may need to be restarted with sterile components. The time consumed by this process can be critical to the success of the procedure. Additionally, when traversing through the heart of a patient, and particularly the ostium, the larger open space of the heart makes identical placement of the supplemental wire guide somewhat difficult.

Accordingly, there exists a need to provide a supporting wire guide for intracorporeal procedures that may be easily and reliably traversed through the vasculature to a position proximate a previously introduced wire guide.

BRIEF SUMMARY OF THE INVENTION

The present invention provides a supporting wire guide for intracorporeal procedures that may be easily and reliably traversed through a body lumen to a position proximate a previously introduced wire guide. The supporting wire guide is a coupling wire guide that is structured to be slidably coupled to the previously introduced wire guide. In one embodiment constructed in accordance with the teachings of the present invention, the coupling wire guide generally includes a main body and a tip portion connected to the distal end of the main body. The tip portion includes a coupling head defining a coupling passageway. The coupling head is operable between at least two positions including a first position generally aligned with the main body and a second position non-aligned with the main body.

According to more detailed aspects of the invention, the tip portion is preferably constructed of a resilient material, and most preferably a plastic overmolded onto the distal end of the main body. The tip portion includes a neck connected to the coupling head which flexes to permit the coupling head to transition between the first and second positions. The neck has an outer diameter that is less than the outer diameter of the coupling head, and preferably includes one or more radially facing depressions to create a predetermined path along which the coupling head flexes between the first and second positions. An outer diameter of the coupling head is about equal to or less than the largest diameter of the remainder of the tip portion, thereby improving placement and translation of the coupling wire guide when not coupled to a previously introduced wire guide.

According to another aspect of the invention, the coupling head is biased towards the first position. The coupling passageway is generally parallel to the distal end of the main body in the second position to promote smooth translation along the previously introduced wire guide. The coupling passageway defines a passageway axis while the main body includes a central axis. In the first position, the passageway axis is angled relative to the central axis, and in the second position, the passageway axis is generally parallel with the central axis. Preferably, the passageway axis is angled less than 45 degrees relative to the central axis when in the first position.

BRIEF DESCRIPTION OF THE DRAWINGS

The accompanying drawings incorporated in and forming a part of the specification illustrate several aspects of the present invention, and together with the description serve to explain the principles of the invention. In the drawings.

DETAILED DESCRIPTION OF THE INVENTION

Figure 1:
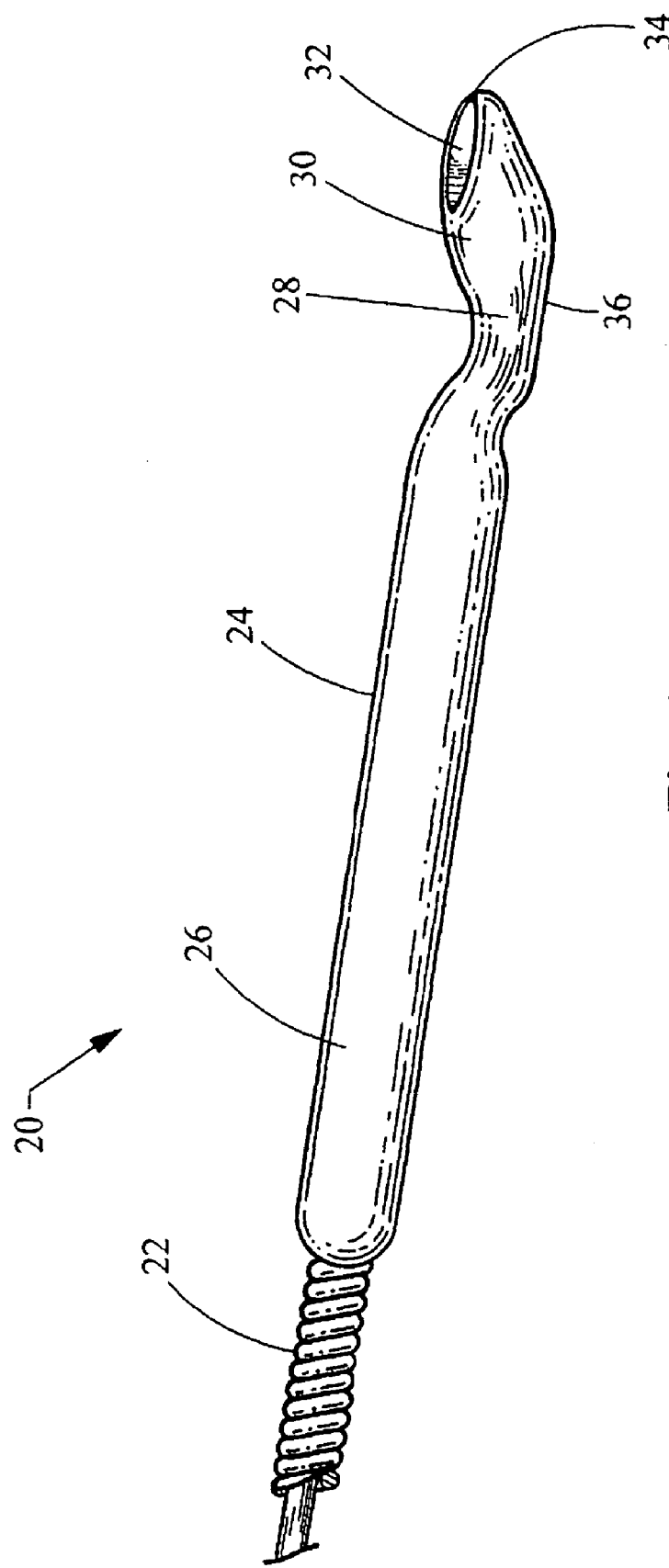
FIG. 1 is a perspective view of a coupling wire guide constructed in accordance with the teachings of the present invention.
Figure 2:
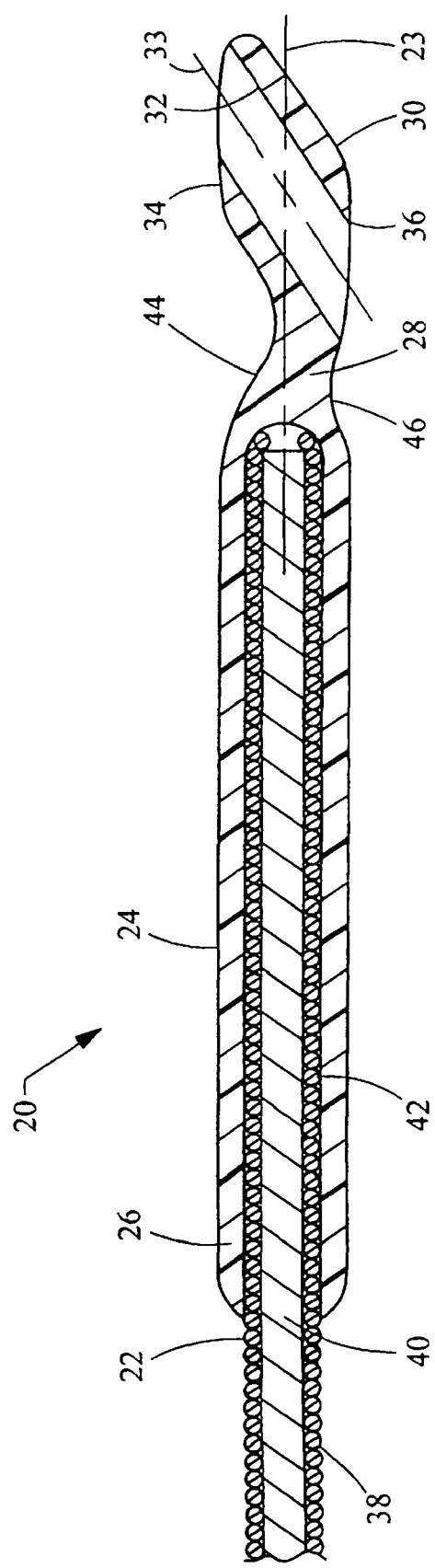
FIG. 2 is a cross-sectional view of the coupling wire guide shown in FIG. 1.
Figure 3:
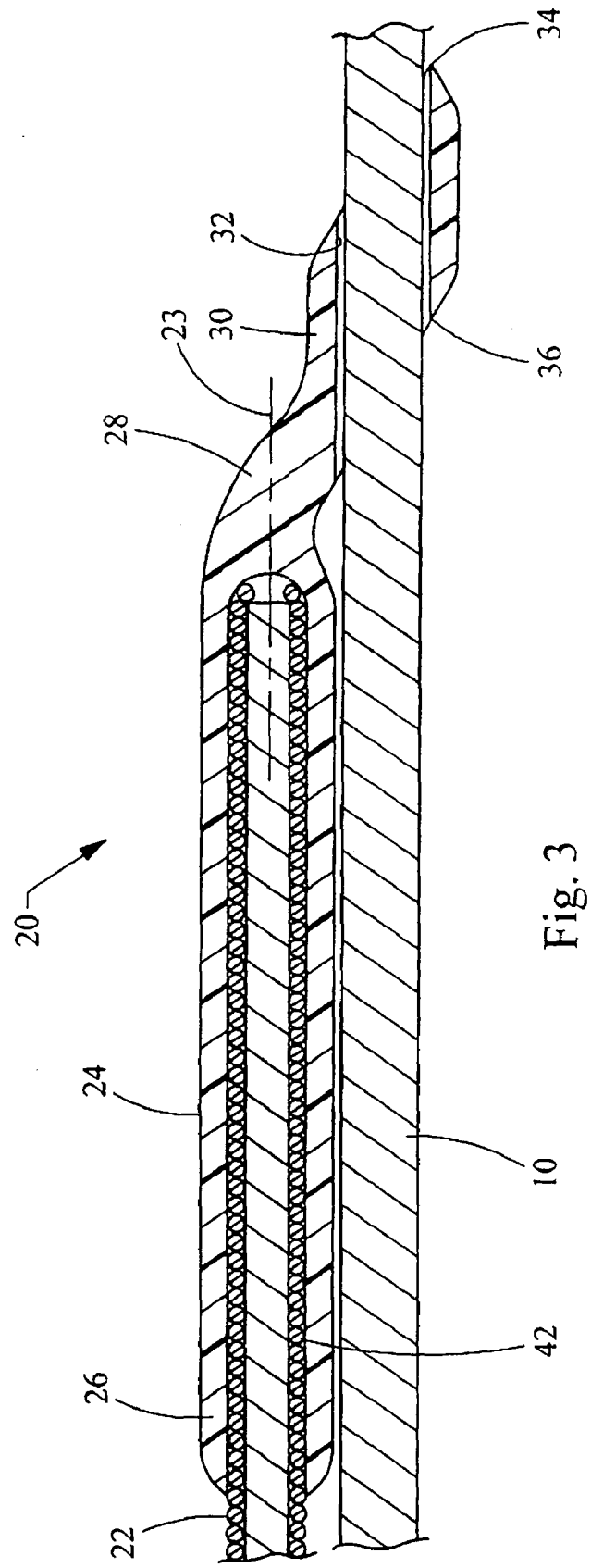
FIG. 3 is another cross-sectional view of the coupling wire guide shown in FIG. 1.

Turning now to the figures, FIGS. 1 to 3 depict a coupling wire guide 20 constructed in accordance with the teachings of the present invention. The coupling wire guide 20 is easily and reliably coupled to and traversed along a previously introduced wire guide 10, and also is easily used alone by maintaining a relatively low profile when decoupled. While wire guides are generally used in percutaneous interventional procedures, it will be recognized by those skilled in the art that the wire guide of the present invention may also be employed non-percutaneously, such as in endoscopic or other intracorporeal procedures. As best seen in FIG. 1, the coupling wire guide 20 generally includes a main body 22 and a tip portion 24. The tip portion includes an attachment section 26, a neck 28 and a coupling head 30. The coupling head 30 defines a lumen having an elongated coupling passageway 32 extending between a distal port 34 and a proximal port 36 through which the previously introduced wire guide 10 passes, as shown in FIG. 3.

As best seen in FIGS. 2 and 3, the main body 22 generally comprises a coiled wire 38 disposed over a mandrel 40, a structure well known in the art. It will be recognized that the previously introduced wire guide 10, as well as the main body 22 of the coupling wire guide 20, may take numerous forms as many types of wire guides are known in the art, including solid wire, tubular wires, coiled wires and combinations thereof. For example, U.S. Pat. No. 5,243,996 discloses an exemplary solid wire mandrel having a coil tip section.

A distal end 42 of the main body 22 is connected to the attachment section 26 of the tip portion 24. The methods and materials used to inter-connect attachment section 26 and distal end 42 will vary depending upon the configuration and type of material utilized for the main body 22 and the tip portion 24. In the figures, the tip portion 24 and its attachment section 26 have been depicted as a plastic material, and preferably a biocompatible thermoplastic which may be injection molded. Preferable materials include polytetrafluoroethylene (PTFE), expanded polytetrafluoroethylene (EPTFE), polyethylene ether ketone (PEEK), polyvinylchloride (PVC), polyamide including Nylon®, polyimide, polyurethane, polyethylene (high, medium or low density), and elastomers such as Santoprene®, including multi-layer or single layer constructions with or without reinforcement wires, coils or filaments. In this manner, the attachment section 26 may be overmolded directly onto the distal end 42 of the main body 22. It will be recognized that in the overmolding process, the plastic material forming the attachment section 26 will be allowed to flow in between and around the coils of wire 38 to provide a secure inter-connection of the main body 22 and tip portion 24.

As noted above, many different attachment methods and materials may be used depending on the particular materials utilized. For example when the tip portion 24 is formed of a metal such as stainless steel or nitinol (Ni—Ti superelastic alloy), or when the attachment section 26 is formed of this material, the attachment section 26 may be soldered or welded to the distal end 42, or may inter-connected through other mechanical means such as clamping, latching, fasteners, material deformation techniques and the like.

The tip portion 24 includes a neck 28 linking the attachment section 26 to the coupling head 30. The neck 28 preferably includes a first radially facing depression 44 and a second radially facing depression 46. The neck thus has an outer diameter less than an outer diameter of the coupling head 30. The neck 28 is constructed of a resilient but flexible material such that the coupling head 30 may take a decoupled or unbiased first position depicted in FIG. 2, but yet may be rotated, pivoted, or otherwise transitioned from this natural state to a biased second position depicted in FIG. 3. The shape of the neck 28 and particularly the depressions 44, 46 assist in providing this flexibility and determining the path of transition between the first and second positions depicted in FIGS. 2 and 3, respectively. Specifically, these depressions 44, 46 may take various sizes and shapes to determine the path followed by the head 30 between the first and second positions.

Generally, the coupling head 30 is aligned with the main body 22 in the first position (FIG. 2), and is generally non-aligned (and offset from) the main body 22 in the second position (FIG. 3). That is, the coupling head 30 is generally in-line with a central axis 23 of the main body 22 in the first position, but is positioned radially away from the central axis 23 in the second position. The first depression 44 faces away from the second position (FIG. 3) of the coupling head 30, while the second depression 46 faces towards the second position of the coupling head 30. Due to the resilient nature of the neck 28 and coupling head 30, the coupling head 30 generally returns to the first position when decoupled from a previously introduced wire guide 10. Further, the outer diameter of the coupling head 30 is about equal to or less than the largest diameter of the remainder of the tip portion 24, namely the attachment section 26. As such, the coupling wire guide 20 is easily used as a single wire guide having a coupling tip portion 24 that is generally aligned with the main body 22 while maintaining a consistent profile or outer diameter.

Notably, in the second position (FIG. 3), the coupling passageway 32 takes a position which eases transition of the coupling wire guide 20 along the previously introduced wire guide 10. It can be seen that the coupling passageway 32 is positioned radially outside the distal end 42 of the main body 22 in the second position. In the first position (FIG. 2), the coupling passageway 32 defines a passageway axis 33 which is angled relative to the central axis 23 of the main body 22. Preferably, this angle is less than 45 degrees and most preferably about 15 to 30 degrees such that the coupling head 30 only needs to rotate about 45 degrees or less to the second position. In the coupled or second position shown in FIG. 3, the passageway axis 33 is generally parallel with the central axis 23 of the main body 22. By the term generally parallel, it is meant that the axes or bodies are parallel within 5 degrees of one another. In this manner, the previously introduced wire guide biases the tip portion 24, which bends to meet the previously introduced wire guide 10, rather than forcing the previously introduced wire guide 10 to itself bend into the passageway 32 formed by the previously introduced wire guide 20. Accordingly, the coupling wire guide 20 may be translated in a generally parallel fashion along the previously introduced wire guide 10 while minimizing any deformation or bending of the previously introduced wire guide 10.

Figure 4:
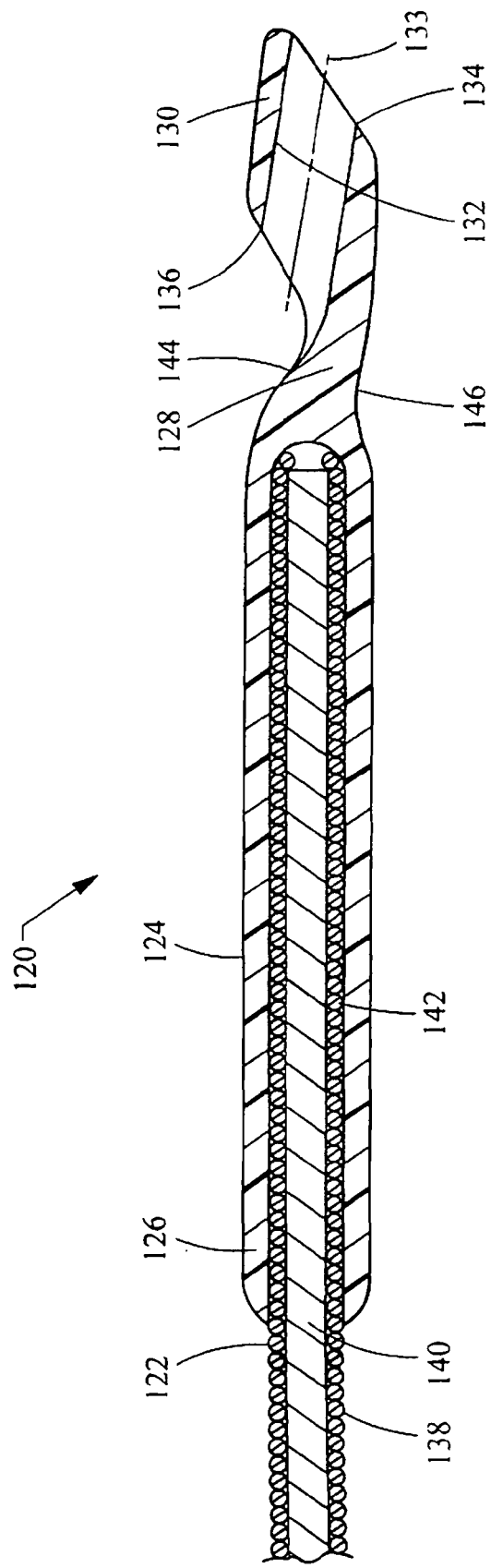
FIG. 4 is a cross-sectional view of another coupling wire guide constructed in accordance with the teachings of the present invention.
Figure 5:
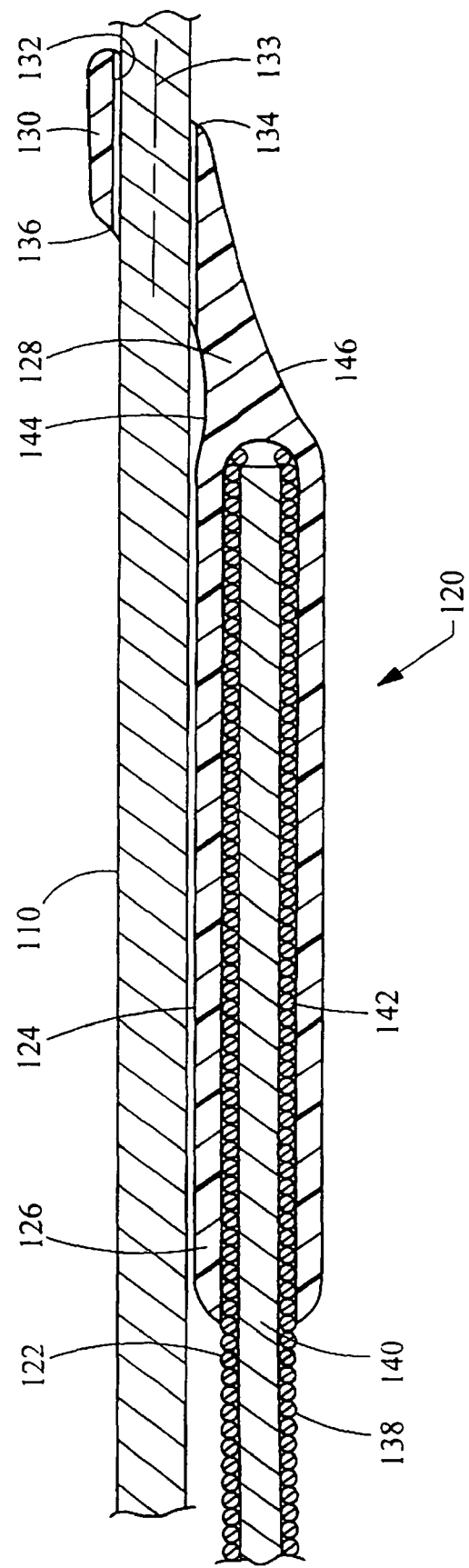
FIG. 5 is a different cross-sectional view of the coupling wire guide shown in FIG. 4.

Another embodiment of a coupling wire guide 120 is depicted in FIGS. 4 and 5. Similar to the prior embodiment, the coupling wire guide 120 includes a main body 126 and a tip portion 124. The tip portion 124 includes an attachment section 126, a neck 128 and a coupling head 130 which transitions between a first position depicted in FIG. 4 and a second coupling position depicted in FIG. 5. The coupling head 130 defines a coupling passageway 132 having an axis 133 which is angled relative to the central axis of the main body 122 in the first position, but generally parallel to the central axis in the second position. The main body 122 again includes an outer wire 138 disposed over a inner mandrel 140, and having a distal end 142 which is connected to the attachment section 126 of the tip portion 124.

In this embodiment of the coupling wire guide 120, the neck 128 includes first and second depression 144, 146 much like the prior embodiment, however the first depression 144 generally faces the second position of the coupling head 130. That is, the coupling passageway 132 opens towards the larger first depression 144, thereby providing greater access to the proximal port 136. At the same time, the neck 128 must provide greater flexibility and the coupling head 130 must bend a bit more than the prior embodiment, although the angled rotation of the passageway 132 is somewhat less than the prior embodiment. It will be recognized by those skilled in the art that numerous embodiments of the present invention are possible, both through the use of materials different than those described here, as well as through numerous shapes and orientations of the coupling tip and its pivoting head.

Figure 6:
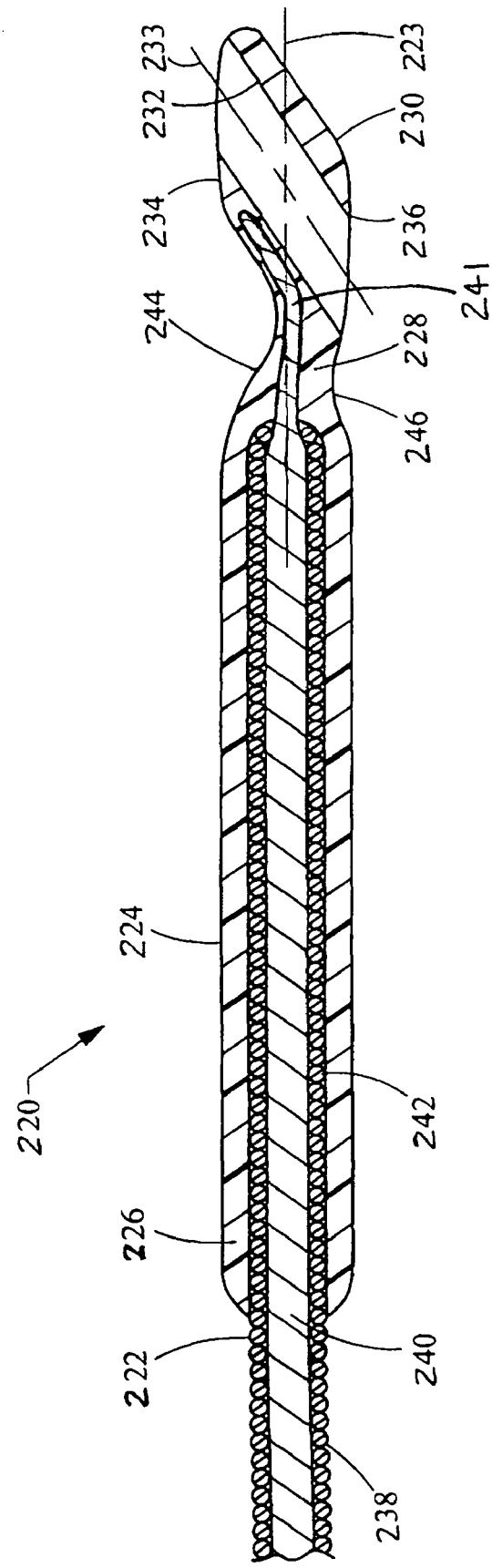
FIG. 6 is a cross-sectional view of another coupling wire guide constructed in accordance with the teachings of the present invention.
Figure 7:
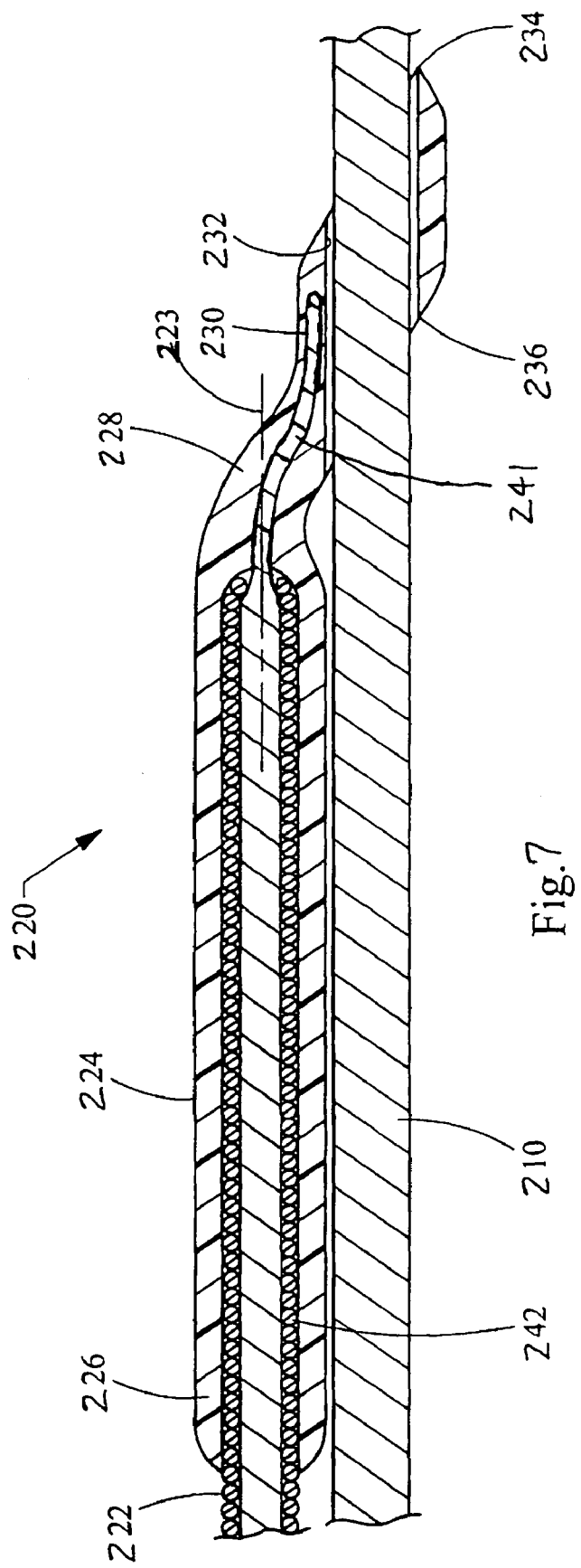
FIG. 7 is a different cross-sectional view of the coupling wire guide shown in FIG. 6.

Another embodiment has been depicted in FIGS. 6 and 7. As with the previous embodiments, the coupling wire guide 220 generally includes a main body 222 and a tip portion 224. The tip portion 224 includes an attachment section 226, a neck 228 and a coupling head 230. The coupling head 230 defines a coupling passageway 232 having a distal port 234 and a proximal port 236 through which the previously introduced wire guide 210 passes, as shown in FIG. 7. The main body 222 of the coupling wire guide 220 generally comprises a coiled wire 238 disposed over a mandrel 240. A distal end 242 of the main body 222 is connected to the attachment section 226 of the tip portion 224. The neck 228 of the tip portion 224 links the attachment section 226 to the coupling head 230. The neck 228 again includes a first radially facing depression 244 and a second radially facing depression 246.

In this embodiment, the neck 228 is reinforced with a securing member 241. As shown, the securing member 241 is an extension of the mandrel 240. That is, the distal end of the mandrel 240 has been formed with a reduced diameter portion that protrudes beyond the outer coiled wire 238, and over which the tip portion 224 is formed. As shown, the securing member 241 extends through the neck 228, along side the coupling passageway 232, and partially into the coupling head 230. The securing member 241 is structured (such as through sizing or material selection) to retain the flexible nature of the neck 228 and permit transition between the first decoupled position (FIG. 6) and the second coupled position (FIG. 7), while at the same time providing additional strength to the neck 228 and passageway 232.

It will be recognized by those skilled in the art that the securing member 241 may take many forms. For example, the outer wire 238 could be extended into the neck 228 and/or coupling head 230 instead of the mandrel 240. Further, rather than unitarily forming the securing member 241 as an extension of the main body 222, the securing member 241 may be separately formed and attached to either the mandrel 240 and/or the outer wire 238, or not attached at all. When separately formed, the securing member 241 can be made of various metals, alloys, plastics or combinations thereof (e.g., a plastic could be selected that is stiffer or stronger than that used for the coupling tip). As previously discussed, the main body 222 can take many forms, and likewise the securing member 241 may also take many forms and shapes.

The coupling wire guide of the present invention provides secure coupling to a previously introduced wire guide with easy and reliable translation along the previously introduced wire guide. At the same time, the wire guide has an uncoupled position where the coupling tip maintains an aligned and generally low profile to improve maneuverability of the coupling wire guide when decoupled. In the coupled mode, the tip portion itself bends to permit the coupling wire guide and previously introduced wire guide to be aligned generally and parallel for smooth translation of the two guides relative to one another. In this manner, the previously introduced wire guide does not need to bend or deform in order to couple and translate the two wire guides relative to one another.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A coupling wire guide for coupling to a previously introduced wire guide during intracorporeal procedures, the coupling wire guide comprising:
 a main body having a distal end; and
 a tip portion connected to the distal end of the main body, the tip portion including a coupling head defining a coupling lumen having an elongated passageway, the coupling head operable between at least two positions including,
  a first unbiased position generally aligned with the main body and having the coupling lumen defining a lumen axis, substantially all of the lumen axis being generally non-parallel to the distal end, and
  a second biased position generally non-aligned with the main body and having the axis of the coupling lumen being generally parallel to the distal end of the main body, the previously introduced wire guide passing through the coupling lumen and biasing the coupling head towards the second biased position.

2. The coupling wire guide of claim 1, wherein an outer diameter of the coupling head is about equal to or less than the largest diameter of the tip portion.

3. The coupling wire guide of claim 1, wherein the natural state of the coupling head is the first position.

4. The coupling wire guide of claim 1, wherein the tip portion is constructed of a resilient material.

5. The coupling wire guide of claim 1, wherein the coupling head is designed to follow a predetermined path between the first and second positions.

6. The coupling wire guide of claim 1, wherein the tip portion includes a neck connected to the coupling head, the neck flexing to permit the coupling head to transition between the first and second positions.

7. The coupling wire guide of claim 6, further comprising a securing member extending into the neck.

8. The coupling wire guide of claim 7, wherein the securing member is defined by a reduced diameter portion of the main body.

9. The coupling wire guide of claim 6, wherein the neck has an outer diameter less than an outer diameter of the coupling head.

10. The coupling wire guide of claim 6, wherein the neck includes a first radially facing depression, the first depression facing away from the second position of the coupling head.

11. The coupling wire guide of claim 1, wherein the tip portion further includes an attachment section fixedly connected to the main body.

12. The coupling wire guide of claim 11, wherein the attachment section is a sleeve engaging the main body.

13. The coupling wire guide of claim 1, wherein the tip portion is unitarily formed as a single piece connected to the distal end of the main body.

14. A coupling wire guide for coupling to a previously introduced wire guide during intracorporeal procedures, the coupling wire guide comprising:
a main body having a distal end; and
a tip portion connected to the distal end of the main body, the tip portion including a coupling head defining a coupling lumen, the coupling head operable between at least two positions including,
a first unbiased position generally aligned with the main body and having the coupling lumen defining an axis generally non-parallel to the distal end, and
a second biased position generally non-aligned with the main body and having the axis of the coupling lumen being generally parallel to the distal end of the main body, the previously introduced wire guide passing through the coupling lumen and biasing the coupling head towards the second biased position,
wherein the tip portion includes a neck connected to the coupling head, the neck flexing to permit the coupling head to transition between the first and second positions, the neck including a first radially facing depression facing away from the second position of the coupling head, the neck including a second radially facing depression facing towards the second position of the coupling head, the second depression being smaller than the first depression.

15. The coupling wire guide of claim 14, wherein the neck is solid.

16. the coupling wire guide of claim 14, wherein the neck includes the first and second depressions in the first unbiased position.

17. The coupling wire guide of claim 14, wherein the coupling lumen defines proximal and distal ports in an exterior surface of the coupling head.

18. A coupling wire guide for coupling to a previously introduced wire guide during intracorporeal procedures, the coupling wire guide comprising:
a main body having an outer coiled wire defining a distal end of the main body; and
a tip portion connected to the distal end of the main body, the tip portion including an attachment section and a coupling head, the attachment section connected to the main body, the attachment section being formed of a plastic material and injection molded over the distal end of the main body, the plastic material flowed in between and around coils of the outer coiled wire, the coupling head defining a coupling passageway_sized to receive the previously introduced wire guide, the coupling head movable relative to the attachment section and operable between at least two positions including,
a first position generally aligned with the main body and having the coupling passageway defining a lumen axis, substantially all of the lumen axis being generally non-parallel to the distal end, and
a second position generally non-aligned with the main body.

19. A coupling wire guide for coupling to a previously introduced wire guide during intracorporeal procedures, the coupling wire guide comprising:
a main body having a distal end and defining a central axis; and
a tip portion fixedly connected to the distal end of the main body, the tip portion including a coupling head and a neck formed of a flexible material, the coupling head having a coupling lumen having an elongated passageway defining a lumen axis the lumen axis being a substantially straight line axis, the coupling lumen sized to receive the previously introduced wire guide the coupling head operable between at least two positions including,
a first position wherein the lumen axis is angled relative to the central axis, and
a second position wherein the lumen axis is generally parallel with the central axis and the coupling head is moved radially away from the central axis,
the neck flexing to permit the coupling head to transition between the first and second positions.

20. The coupling wire guide of claim 19, wherein the coupling head is generally aligned with the main body in the first position.

21. The coupling wire guide of claim 19, wherein the coupling head is generally non-aligned with the distal end of the main body in the second position.

22. The coupling wire guide of claim 19, wherein an outer diameter of the coupling head is about equal to or less than the largest diameter of the tip portion.

23. The coupling wire guide of claim 19, wherein the natural, unbiased position of the coupling head is the first position.

24. The coupling wire guide of claim 19, wherein the lumen axis is angled less than 45 degrees relative to the central axis.

25. The coupling wire guide of claim 19, wherein the neck has an outer diameter less than an outer diameter of the coupling head.

* * * * *